United States Patent [19]

Caulder et al.

[11] Patent Number: 4,775,405
[45] Date of Patent: Oct. 4, 1988

[54] SYNERGISTIC HERBICIDAL COMPOSITIONS COMPRISING COLLETOTRICHUM TRUNCATUM AND CHEMICAL HERBICIDES

[75] Inventors: Jerry D. Caulder, San Diego, Calif.; Larry Stowell, San Diego, Calif.

[73] Assignee: Mycogen Corporation, San Diego, Calif.

[21] Appl. No.: 784

[22] Filed: Jan. 6, 1987

Related U.S. Application Data

[62] Division of Ser. No. 747,511, Jun. 21, 1985, abandoned.

[51] Int. Cl.$^4$ ............................................. A01N 63/00
[52] U.S. Cl. .......................................... 71/79; 71/116; 71/91; 71/94; 71/103
[58] Field of Search ....................... 71/79, 116, 91, 94, 71/103

[56] References Cited

U.S. PATENT DOCUMENTS

| | | | |
|---|---|---|---|
| 3,849,104 | 11/1974 | Daniel et al. | 71/79 |
| 4,549,903 | 10/1985 | Gerhold | 71/116 |
| 4,643,756 | 2/1987 | Cardina et al. | 71/79 |

OTHER PUBLICATIONS

Charudattan, R., Walker, H. L., *Biological Control of Weeds with Plant Pathogens*, John Wiley & Sons, 1982, p. 30–34.
Quimby, P. C., "Applying Alternarra Cassiae to Sicklepod", Proceedings from the Southwest Weed Science Soc., vol. 36, p. 473–474 Jan 18, 1983.
Smith, Jr., "Integration of Microbial Herbicides w. Exist. Pest Manag." *Biological Control of Weeds w. Plant Pathogens*, Chpt 12, Wiley & Sons, 1982.

*Primary Examiner*—Richard L. Raymond
*Attorney, Agent, or Firm*—Roman Saliwanchik; David R. Saliwanchik

[57] ABSTRACT

Disclosed are compositions and processes for controlling undesirable weeds. These compositions comprise synergistic combinations of colletotrichumtruncatum and chemical herbicides. Use of the synergistic compositions of the subject invention enhances the value of the microbial herbicide by reducing the amount of microbial herbicide needed and by extending the range of environmental conditions in which the microbial herbicide will function.

10 Claims, No Drawings

SYNERGISTIC HERBICIDAL COMPOSITIONS COMPRISING COLLETOTRICHUM TRUNCATUM AND CHEMICAL HERBICIDES

The present application is a divisional application of co-pending application Ser. No. 747,511, filed on June 21, 1985 now abandoned.

BACKGROUND OF THE INVENTION

Weeds cost farmers billions of dollars annually in crop losses and in the expense of keeping the weeds under control. Much of the cost of intertillage of row crops, maintenance of fallow, seedbed preparation, and seed cleaning is chargeable to weed control. Another expensive item is suppression of weeds along highways and railroad right-of-ways, and in irrigation ditches, navigation channels, yards, parks, grounds, and home gardens. Ragweed pollen is the source of annual periodic distress to several million hay fever sufferers. Poison ivy, poison oak, poison sumac, nettles, thistles, sandburs, and puncturevine also bring pain to millions. The barberry bush, which spreads the black-stem rust of grains and grasses, can be regarded as a weed. Weeds also serve as hosts for other crop diseases as well as for insect pests.

The losses caused by weeds in agricultural production environments include decrease in crop yield, reduced crop quality, increased irrigation costs, increased harvesting costs, decreased land value, injury to livestock, and crop damage from insects and diseases harbored by the weeds.

Chemical herbicides have provided an effective method of weed control in the past. However, the public has become concerned about the amount of chemicals applied to the food that they consume, to the land on which they live, and to the ground water which they use. Stringent restrictions on the use and development of new herbicides and the elimination of some effective herbicides from the market place have limited economical and effective means for controlling costly weed problems.

A problem has been identified after years of use of chemical herbicides on commercial agricultural land, i.e., the lack of control of certain weeds has allowed these weeds to take over the areas where, without the use of chemical herbicides, they were excluded by more hardy weeds. Removal of the more competitive weeds with chemical herbicides has left an ecological void that has been filled by the less competitive weeds that are resistant to the herbicides. Weeds that were of minor importance at one time have spread rapidly throughout the areas where they are found and are now considered major weed problems. In addition to the inadequacy of control of all weeds, chemicals also can damage the crop plants, sometimes injure nontarget organisms in the environment, and can leave undesirable residues in water and harvested products and carry-over in subsequent crops.

Microbial herbicides are plant pathogens which are effective, when used according to the process disclosed herein, in controlling weeds or other undesirable vegetation without adversely affecting the growth and yield of the desired field crop. The composition of a microbial herbicide includes spores or cells of the plant pathogen or any portion of the organism that is capable of infecting the weed. The use of microbial herbicides is becoming an increasingly important alternative to chemical herbicides. This importance is accompanied by the issuance of several patents for microbial herbicides and their use. Some of these patents, by way of illustration, are as follows: U.S. Pat. No. 3,849,104 (control of northern jointvetch with *Collectotrichum gloeosporioides Penz. aeschynomene*); U.S. Pat. No. 3,999,973 (control of prickly sida [teaweed] and other weeds with *Collectotrichum malvarum*); U.S. Pat. No. 4,162,912 (control of milkweed vine with *Araujia mosaic* virus); U.S. Pat. No. 4,263,036 (control of *Hydrilla verticillata* with *Fusarium roseum* Culmorum); U.S. Pat. No. 4,390,360 (control of sicklepod, showy crotalaria, and coffee senna with *Alternaria cassiae*); and U.S. Pat. No. 4,419,120 (control of prickly sida, velvetleaf, and spurred anoda with fungal pathogens).

Microbial herbicides have been developed specifically for control of weeds which are not adequately controlled by chemical herbicides. Examples include *Collectotrichum gloeosporioides f.sp. aeschynomene* for control of northern jointvetch in rice; *Alternaria cassiae* for control of sicklepod in soybeans, cotton, and peanuts; and *Fusarium lateritium* for control of velvetleaf in soybeans. In each of these cases the weed is not effectively controlled by the chemical herbicides currently labeled for use in the respective cropping system. The factors currently limiting in commercialization of microbial herbicides are the high cost of production, limited spectrum of weed control, and the narrow range of environmental conditions in which these pathogens will infect the host.

The effects of herbicides on plant diseases was recently reviewed by Altman (Altman, J. and Campbell, L. C. [1977] Ann. Rev. Phytophathol. 15:373-375). Altman reported that herbicides may either increase or reduce plant disease and severity. There are five major herbicide effects which may lead to increased disease: (a) a reduction in the biochemical defenses of the host against the pathogen; (b) reduction of structural defenses of the host; (c) stimulation of increased exudation from host plants; (d) stimulation of pathogen growth and/or production of chemicals which damage the plant; and (e) inhibition of microflora competing with potential pathogens. There are four major effects of herbicides which lead to decreased disease incidence and/or severity: (a) increased host biochemical defenses; (b) increased host structural defenses; (c) stimulation of microflora competing with potential pathogens; and (d) a decrease in either the pathogen's growth or its production of chemicals which are damaging to plants. At the current state of chemical herbicide and microbial herbicide art, there is no method of predicting the interaction (neutral, antagonistic, or synergistic) between a microbial herbicide and a chemical herbicide in controlling a specific weed or unwanted vegetation.

Prior art in the area of microbial herbicide and chemical herbicide interactions indicates that foliar application of mixtures of a microbial herbicide and a chemical herbicide results in antagonism and reduced efficacy of the microbial herbicide. Plant pathogens can break down chemical herbicides and chemical herbicides can be fungicidal (Wilson, C. L. [1969] Ann. Rev. Phytopathol. 7:424). Examples of positive interactions between microbial herbicides and chemical herbicides require that the microbial herbicide be applied either before or after the application of the chemical herbicide (Klerk, R. A., Smith, Jr., R. J. and TeBeest, D. O. [1985] Weed Science 33:95-99). Multiple applications of pest control products is expensive and commercially undesirable.

The commercially viable methods for the application of a combination product (such as a microbial herbicide and a chemical herbicide) are a "tank mix," and a "package mix." Tank mixing is a process by which two or more components of a pest control program are added to the same spray tank and this mixture is applied to the field. The components may be packaged together (package mix) or separately (tank mix) but the components must be compatible when added to the spray tank. Mixtures are applied to the field with one application. Applying a mixture reduces fuel consumption, machinery wear, and operator time; and preserves the soil texture by reducing soil compaction. At this stage in the herbicide art there is no known way to predict success, if any, in combining a chemical herbicide with a microbial herbicide.

We have discovered that mixtures of microbial herbicides and chemical herbicides, and some chemical plant growth regulators, are synergistic in their activity when applied to the foliage of the host weed of the microbial herbicide. This is the first report of synergy between microbial herbicides and chemical herbicides applied as mixtures. This synergy will greatly increase the value of microbial herbicides by reducing the amount of microbial herbicide applied, reducing the environmental limitations of the microbial herbicide, and increasing the spectrum of weed control of some herbicide treatments.

BRIEF SUMMARY OF THE INVENTION

The subject invention concerns the unexpected discovery that certain mixtures of microbial herbicides and chemical herbicides, and some chemical plant growth regulators, produce a synergistic effect against target weeds. This synergistic effect significantly enhances the value of the microbial herbicide by reducing the amount of microbial herbicide needed and by extending the range of environmental conditions in which the microbial herbicide will function. Specifically, by using the microbial herbicides and chemical herbicides disclosed herein, in mixture, there is obtained, advantageously, a synergistic effect resulting in kill or suppression of previously uncontrolled weeds or other vegetation.

The activity of a microbial herbicide is sensitive to fluctuations in the environment. The majority of the examples which support our discoveries were carried out under greenhouse conditions. The environmental conditions within the greenhouse are more constant than the ambient environment outside the greenhouse. However, the environment within the greenhouse fluctuates daily and the interaction between a microbial herbicide and its host also varies with these changes in environment. The sensitivity of microbial herbicides to environmental fluctuations is one of the major constraints in commercializing a microbial herbicide. This sensitivity to environment explains the lack of consistent control when the same rate of microbial herbicide was applied to weeds on different days. This sensitivity to environment is reduced when the microbial herbicide is combined with a chemical herbicide. The result is effective weed control under a wide range of environmental conditions.

The discovery of microbial herbicides and chemical herbicides that produce a synergistic effect in controlling a target weed was unexpected. Salts of chemical herbicides (which are organic acids) were discovered to be synergistic when applied as mixtures with microbial herbicides. Not all salts of chemical herbicides demonstrated this synergy with all microbial herbicides. However, all salts of chemical herbicides which are active against broadleaf weeds (see Table 1) when used with the microbial herbicides (which attack broadleaf weeds) were found to be synergistic, and increase the spectrum of control of some herbicide treatments.

Generally, in the practice of the subject invention, the microbial herbicide can be applied at rates between 10E7 to 10E12 propagules per acres, and the chemical herbicide can be applied at rates of $\frac{1}{2}$ to 1/32 the rate recommended for weed control on the label of the compound in accordance with EPA regulations, against the target weed. If desired, the chemical herbicides can be used at recommended full rates to achieve a broader spectrum of weed control.

DETAILED DISCLOSURE OF THE INVENTION

The synergistic mixtures of microbial herbicides and chemical herbicides of the subject invention make possible the control of weeds which cannot be effectively controlled by either the microbial herbicide or the chemical herbicide alone. The most preferred microbial herbicides of the invention are plant pathogens from the genera Alternaria, Collectotrichum, and Fusarium.

Other microbial herbicides of the invention include plant pathogens from the following genera:

| | |
|---|---|
| Acremonium | Monochaeta |
| Ascochyta | Myrothecium |
| Bipolaris | Pestalotia |
| Cephalosporium | Phoma |
| Ceratocystis | Phylosticta |
| Cercospora | Phytophthora |
| Coleosporium | Puccinia |
| Curvularia | Septoria |
| Dichotomophthora | Sphacelotheca |
| Dichotomophthoropsis | Sporosporium |
| Dreschlera | Stemphylium |
| Exserohilum | Uredo |
| Helminthosporium | Verticillium |

Representative species and target weeds of the above genera are as follows:

*Acremonium diospyri* (ATCC 22202,22206)
Weed: *Diospyros virgianiana* L. (persimmon)
*Alternaria cassiae* Jurair and Kahn (NRRL 12533, ATTC 4687)
Weed: *Cassia obtusifolia* L. (sicklepod)
*Alternaria eichhorniae* Nag Raj and Ponnappa (ATTC 22255)
Weed: *Eichhornia crassipes* (Mart.) Solms (water-hyacinth)
*Alternaria helanthi* (Hansford) Tugaki and Nishirara
Weed: *Xanthium strumarium* (heartleaf cocklebur)
*Alternaria macrospora* Zimm. (ATCC 42770)
Weed: *Anoda cristata* (L.) Schlecht. (spurred anoda)
*Alternaria alternantherae* Holcomb and Antonopoulos (ATCC 32833, 44528, 48851)
Weed: *Alternanthera philoxeroides* (Mart.) Griseb. (alligatorweed)
*Ascochyta pteridium* Bres.
Weed: *Pteridium aquilinum* (bracken fern)
*Ceratocystis fagacearum* (Bretz) Hunt (ATCC 24790)
Tree: *Quercus* spp. (red and burr oak)
*Cercospora hydrocotyles* Ellis and Everh. (ATCC 36217)
Weed: *Ipomoea hederacea* (L.) Jacq. (morningglory, ivyleaf)
*Cercospora nymphaeacea* Cooke and Ellis (ATCC 36216)

Weed: *Nuphar luteum* (L.) Sibth. & Sm. (yellow waterlily)
*Cercospora rodmanii* Conway (U.S. Pat. No. 4,097,261)
Weed: *Eichornia crassipes* (Mart.) Solms. (water-hyacinth)
*Colletotrichum coccodes* Wallr. (DAOM 183088)
Weed: *Abutilon theophrasti* Medic. (velvetleaf)
*Colletotrichum coccodes* Wallr. (NRRL 15547)
Weed: *Solanum ptycanthum* (black nightshade)
*Colletotrichum gloeosporioides* (Penz.) f. sp. aeschynomene (ATCC 20358)
Weed: *Aeschynomene virginica* (L.) B.S.P. (northern jointvetch)
*Colletotrichum gloeosporioides* (Penz.) f. sp. jussiaeae (ATCC 52634)
Weed: *Jussiaea decurrens* (Walt.) DC. (winged primrose)
*Colletotrichum malvarum* (A. Braun and Casp) (NRRL 8096)
Weeds: *Sida spinosa* L. (prickly sida) *Abutilon theophrasti* Medic. (velvetleaf)
*Colletotrichum truncatum* (Schw.) Andrus & Moore (NRRL 15933)
Weed: *Desmodium tortuosum* (SW.) DC. (Florida beggarweed)
*Dichotomophthora portulacae* Mehrlich and Fitzpatrick (ATCC 22159)
Weed: *Portulaca oleracea* L. (common purslane)
*Dichotomophthoropsis numphaerum* (Rand) M. B. Ellis (ATCC 32819)
Weeds: *Brasenia schreberi* J. F. Gmel. (watershield) *Nymphaea odorata* Ait. (fragrant waterlily)
*Fusarium lateritium* Nees ex Fr. (NRRL 12552)
Weeds: *Anoda cristata* (L.) Schlecht. (spurred anoda) *Sida spinosa* L. (prickly sida) *Abutilon theophrasti* Medic. (velvetleaf)
*Fusarium oxysporum* Schlect. f. *sp. cannabis* Noviello and Snyder (ATCC 14838)
Weed: *Cannabis sativa* L. (hemp)
*Fusarium oxysporum* f. *sp. perniciosum* (Hept.) Toole (ATCC 12282)
Weed: *Albizia julibrissin* Durazz. (silktree albizia)
*Fusarium solani* App. & Wr. f. sp. *cucurbitae* Snyd. & Hans. (NRRL 52552)
Weed: *Cucurbita texana* (A.) Gray (Texas gourd)
*Phytophthora palmivora* (Butler) Butler (ATCC 52158, 52159)
Weed: *Morrenia odorata* Lindl. (stranglervine)
*Puccinia canaliculata* (Schw.) Lagerh.
Weed: *Cyperus esculentus* L. (yellow nutsedge)
*Puccinia chondrillina*
Weed: *Chondrilla juncea* L. (skeletonweed)

The microbial herbicides of the subject invention are known fungi, as disclosed above. These fungi can be grown and formulated for use as microbial herbicides by procedure well known in the art. For example, the following is a list of disclosures giving growth characteristics for the disclosed fungi: *Alternaria macrospora* Zimm. (ATCC 42770), see Walker, H. L. (1979) Weed Sci. 27:612–614; *Ascochyta pteridium* Bres., see TeBeest, D. O. and Templeton, G. E. (1985) Plant Disease 69:6–10; *Colletotrichum gloeosporioides* (Penz.) f. sp. *aeschynomene* (ATCC 20358), see Daniel, J. T., Templeton, G. E. and Smith Jr., J. (1974) U.S. Pat. No. 3,849,104; *Colletotrichum malvarum* (A. Braun and Casp) (NRRL 8096), see Templeton, G. E. (1976) U.S. Pat. No. 3,999,973; *Fusarium lateritium* Nees ex Fr. (NRRL 12552, see Walker, H. L. (1983) U.S. Pat. No. 4,419,120; *Fusarium solani* App. & Wr. f. sp. *cucurbitae* Snyd. & Hans. (NRRL 52552), see Boyette, C. D., Templeton, G. E. and Oliver, L. R. (1984) Weed Sci. 32:649–655; *Phytophthora palmivora* (Butler) Butler (ATCC 52158, 52159), see TeBeest, D. O. and Templeton, G. E. (1985) Plant Disease (69:6–10; *Puccinia chondrillina* see Hasan, S. and Wapshere, A. J. (1973) Ann. Appl Biol. 74:325–332; *Puccinia canaliculata* (Schw.) Lagerh., see Sutker, E. M. (1983) Phytopathology 73:506; and *Dichotomophthora portulaceae* Mehrlich and Fitzpatrick (ATCC 22159), see Klisiewicz, J. M. et al. (1983) Plant Disease 67:1162.

Four species from three genera, listed above, were selected to exemplify this invention:
*Alternaria cassiae*
*Colletotrichum coccodes*
*Colletotrichum truncatum*
*Fusarium lateritium*

Listed in Table 1 are chemical herbicides which are salts of organic acids.

TABLE 1

| Trade Name[1] | Chemical Name | Common Name |
|---|---|---|
| Alanap (B) | 2-[(1-naphthalenylamino)carbonyl] benzoic acid | naptalam |
| Basagran (B) | Sodium salt of (3-isopropyl-1 H—2,1,3-bentzothiadiazin-4 (3H)—one 2,2-dioxide) | bentazon sodium salt |
| Basta (B & G) | Ammonium-DL-homoalanin-4-yl (methyl) phosphinate | glufonsinate ammonium |
| Blazer (B & G) | Sodium 5-[2-chloro-4-trifluoro methyl)phenoxy]-2-nitrobenzoate | acifluorfen sodium salt |
| Butyrac 200 (B) | 4-(2,4-Dichlorophenoxy)butyric acid | 2,4-DB |
| Cobra (B) | 1-(carboethoxy)ethyl 5-[2-chloro-4-(trifluoromethyl)phenoxy]-2-nitrobenzoate | lactofen |
| DOWPON (G) | 2,2'-dichloropropionic acid | dalapon |
| Fusilade (G) | Butyl(R-S)-2-[4-[[5-(trifluoro-methyl)-2-pyridinyl]oxy]phenoxy] propanoate | fluazifop |
| Hoelon (G) | Methyl 2-[4-(2,4-dichlorophenoxy) phenoxy]propanoate | diclofop methyl |
| Premerge 3 (B & G) | Dinoseb(2-sec-butyl-4,6-dinitro-phenol) as the alkanolamine salts | dinoseb |
| Roundup (B & G) | Isopropylamine salt of N—(phosphonomethyl)glycine | glyphosate |
| Scepter (B) | Ammonium salt of 2-[4,5-Dihydro-4-methyl ethyl)-5-oxo-1H—imidazol-2-yl]-3-quinoline carboxylic acid | AC 252,214 |

[1]The notation in parentheses indicates the activity of the herbicide (B = broadleaf control, G = grass control, and B & G - broadleaf and grass control.

Table 2 lists chemical herbicides representing classes of herbicides which are not organic salts, but some having demonstrated a synergistic interaction when used in combination with a microbial herbicide for control of weeds.

TABLE 2

| Trade name | Chemical Name | Common name |
|---|---|---|
| Classic | 2-((([(4-chloro-6-methox-pyrimidine-2-yl)amino carbonyl] amino sulfonyl))benzoic acid ethyl ester | DPX-F6025 |
| Dual 8E | 2-chloro-N—(2-ethyl-6-methyl-phenyl)-N—(2-methoxy-1-methyl-ethyl)acetamide | metolachlor |
| Poast | 2-[1-(ethoxyimino)butyl]-5[2- | sethoxydim |

TABLE 2-continued

| Trade name | Chemical Name | Common name |
|---|---|---|
| | (ethylthio)propyl]-3-hydroxy-2-cyclohexen-1 one | |
| Sencor | 4-Amino-6-(1,1-dimethylethyl)-3-(methylthio)-1,2,4,-triazin-5(4H)—one | metribuzin |
| Surflan | 3,5-Dinitro-N⁴N⁴—dipropyl-sulfanilamide | oryzalin |

Table 3 discloses a plant growth regulators (PGR). Some have demonstrated a synergistic interaction when used in combination with a microbial herbicide for control of weeds.

TABLE 3

| Trade Name | Chemical Name | Common Name |
|---|---|---|
| B-Nine | Daminozide butanedioic acid mono(2,2-dimethylhydrazide) | Alar |
| Dropp | N—phenyl-N'—1,2,3-thiadiazol-5 yl urea | thidiazuron |
| Embark | Diethanolamine salt of (N—[2,4-dimethyl-5-[[(trifluoromethyl)-sulfonyl]amino]phenyl]acetamide | mefluidide |
| Stik | 1-Naphthaleneacetic acid | NAA |

The effect of chemical herbicides upon the germination or growth of *Alternaria cassiae* (AC), *Colletotrichum coccodes* (CC), and *Colletotrichum truncatum* (CT) was studied by exposing the fungi to the chemical or by amending the fungal growth medium with the chemical herbicides. The concentration of herbicide in the medium was adjusted to be equivalent to the concentration of herbicide which would be present in the application spray tank when the herbicide is applied in 25 gal water per acre. Table 4 lists the low and high recommended rates of application of each chemical used in this disclosure and the corresponding concentration of the chemical (in parts per million [PPM]) in the spray tank when the chemical is applied in 25 gal per acre.

Table 5 summarizes the results of spore germination studies with AC and CT. The fungi were exposed to the herbicides for about 8 hr at the reported concentration in water and then transferred to growth media to determine germination. Percent difference indicates the magnitude and increase or decrease in spore germination after exposure to the chemicals as compared to spores exposed to water only. The range of response of CT (−91% to +27%) was greater than that of AC (−71% to +14%), indicating that CT may be more sensitive to the chemicals than AC.

Table 6 summarizes the results of radial growth studies of CC on media amended with chemical herbicides. The concentration of chemicals in the growth medium was adjusted to equal the concentration of each herbicide in a spray tank when the chemical is applied in 25 gal water per acre. All of the treatments reduced the growth of CC over that of non-amended medium (range −8% to −82%).

TABLE 4

Concentration of herbicides and plant growth regulators in the application tank when the compounds are applied at a carrier rate of 25 gal/A

| Chemical | Low rate (lb ai/A) | Conc. (PPM) | High rate (lb ai/A) | Conc. (PPM) |
|---|---|---|---|---|
| Basagran | 0.75 | 3599 | 1.00 | 4798 |
| Blazer | 0.40 | 1919 | 0.50 | 2399 |
| Classic | 0.02 | 96 | 0.17 | 816 |
| Fusilade | 0.25 | 1200 | 0.50 | 2399 |
| Hoelon | 0.50 | 2399 | 1.25 | 5998 |
| Poast | 0.10 | 480 | 0.50 | 2399 |
| Scepter | 0.10 | 480 | 0.23 | 1104 |
| Sencor | 0.25 | 1200 | 0.50 | 2399 |
| Surflan | 2.00 | 9596 | 4.00 | 19192 |
| B-Nine (PGR) | 0.50 | 2399 | 2.10 | 10076 |
| Dropp (PGR) | 0.10 | 480 | 0.20 | 960 |
| Embark (PGR) | 0.05 | 240 | 1.00 | 4798 |

Note: One pound of active ingredient mixed into 25 gallons of water is equivalent to 4798 ppm.

TABLE 5

The effect of chemical herbicides and plant growth regulators on the germination of spores of *A. cassiae* (AC) and *C. truncatum* (CT). The percentages represent the increased or decreased germination as compared to germination on plates which are not amended with the chemicals.

| Chemical | Low rate (lb ai/A) | Conc. (PPM) | Percent difference AC | Percent difference CT |
|---|---|---|---|---|
| Basagran | 0.75 | 3599 | −15 | −82 |
| Blazer | 0.40 | 1919 | −6 | −9 |
| Classic | 0.02 | 96 | −19 | −42 |
| Fusilade | 0.25 | 1200 | +14 | −25 |
| Hoelon | 0.50 | 2399 | −71 | −91 |
| Poast | 0.10 | 480 | −24 | NG |
| Scepter | 0.10 | 480 | +8 | +27 |
| Sencor | 0.25 | 1200 | +1 | +11 |
| Surflan | 2.00 | 9596 | +6 | +13 |
| B-Nine (PGR) | 0.50 | 2399 | +14 | −12 |
| Dropp (PGR) | 0.10 | 480 | −8 | +2 |
| Embark (PGR) | 0.05 | 240 | −11 | −75 |

Note: "NG" indicates that the spores did not germinate after exposure to the chemical at the rate indicated above.

TABLE 6

Growth of *C. coccodes* on media amended with herbicides or plant growth regulators to a concentration equivalent to that encountered in a spray tank containing the low rate of the chemical and a carrier rate of 25 gal per acre. Colony diameter was measured after 12 days' incubation and is expressed as percent reduction in growth compared to growth on the medium without chemicals added.

| Chemical | Low rate (lb ai/A) | ppm | Percent difference |
|---|---|---|---|
| Basagran | 0.75 | 3599 | −23 |
| Classic | 0.02 | 96 | −11 |
| Dropp (PGR) | 0.10 | 480 | −8 |
| Fusilade | 0.25 | 1200 | −43 |
| Hoelon | 0.50 | 2399 | −82 |
| Poast | 0.10 | 480 | −24 |

The three major steps in plant pathogenesis are germination, penetration, and establishment of the pathogen within the host. Germination and penetration are the most environmentally sensitive stages. The three genera of fungi used as examples in this disclosure are representative of two methods of penetration observed in plant pathogenic fungi. Fusarium and Alternaria spp. penetrate passively through open stomates, lenticels, or wounds in the plant surface; Colletotrichum spp. penetrate in the plant surface; Colletotrichum spp. penetrate actively after formation of appressoria (specialized structures which attach to the host surface and release enzymes which dissolve the cuticle and wall materials, allowing penetration of the infective hyphae) and through wounds in the plant surface. The possible interaction of chemical herbicides and the infection process of plant pathogenic fungi is discussed in the Examples.

The results of synergy experiments are summarized in Table 7. A detailed explanation of each experiment is disclosed in the Examples which follow. Salts of chemical herbicides which are active against broadleaf plants provided synergistic activity when applied in a mixture with the microbial herbicide which is active on the broadleaf weed.

Basagran, Blazer, and Scepter are broadleaf chemical herbicides which are salts of organic acids. These herbicides were synergistic with all of the microbial herbicides tested. Hoelon and Fusilade are also salts of organic acids. Hoelon and Fusilade are active against grasses and not against broadleaf weeds or sedges. Hoelon does not have herbicidal activity against broadleaf weeds and would therefore not be expected to be synergistic when combined with a microbial herbicide active against broadleaf weeds. Hoelon is not synergistic when used in combination with *C. truncatum* for control of Florida beggarweed. Hoelon was, unexpectedly, synergistic with *A. cassiae* in control of sicklepod. Fusilade, on the other hand, was synergistic when combined with either *A. cassiae* or *C. truncatum* in control of their respective weed hosts.

TABLE 7

| | Synergy with | | | |
|---|---|---|---|---|
| Chemical | AC | CC | CT | FL |
| Basagran | + | + | + | + |
| Blazer | + | + | + | + |
| Classic | − | + | − | |
| Fusilade | + | | + | |
| Hoelon | + | | − | |
| Poast | + | | − | |
| Scepter | + | | + | |
| Sencor | + | | − | |
| Surflan | + | | + | |
| Dropp (PGR) | − | + | + | |
| B-Nine (PGR) | − | | + | |
| Embark (PGR) | + | | + | |

The suppliers for the above chemical herbicides and plant growth regulators are as follows:

| Trade Name | Supplier |
|---|---|
| Alanap | Uniroyal Chemical |
| Basagran | BASF Wyandotte Corp. |
| Basta | American Hoechst |
| Blazer | Rohm and Haas |
| B-Nine | Uniroyal Chemical |
| Butyrac 200 | Union Carbide |
| Classic | Dupont |
| Cobra | PPG Industries |
| DOWPON | Dow Chemical |
| Dropp | NORAM |
| Dual 8E | Ceiba Geigy |
| Embark | 3M |
| Fusilade | ICI Americas Inc. |
| Hoelon | American Hoechst |
| Paraquat | Chevron |
| Poast | BASF Wyandotte Corp. |
| Premerge 3 | Dow Chemical |
| Roundup | Monsanto |
| Scepter | American Cyanimide |
| Sencor | Mobay Chemical |
| Stik | Union Carbide |
| Surflan | Elanco Products |

The objective of formulating herbicides is to provide the correct combination of ingredients so that the active component is suitable for application and optimum activity. Microbial herbicides have been formulated as dusts, wettable powders, granules, and suspensions.

Wettable powder formulas of Colletotrichum, Alternaria, and Fusarium are composed of a diluent, wetting agent, and dispersant. Wetting agents and dispersants are surface active agents (surfactants) which reduce surface tension and promote homogenous distribution during application. A comprehensive list of surfactants is found in McCutcheon's Emulsifiers & Detergents 1985. Three to five percent of each is needed in the formula to insure performance of the microbial herbicide. The diluents modify the formula to improve handling, storage, and application. Diluents that have been mixed with microbial herbicides are clays (attapulgite, montmorilonite, kaolinite), non-phyllosilites (talc, diatomaceous earth, vermiculite, synthetic bulking agents) and botanicals (grain flours, ground plant parts).

The formulation and application of the chemical herbicides, disclosed herein, are well known to those skilled in the art. See Herbicide Handbook of the Weed Science Society of America, Fifth Edition, 1983. This handbook is published by Weed Science Society of America, 309 West Clark Street, Champaign, Ill. 61820. Also, instructions for the formulation and use of individual chemical herbicides are disclosed on the product labels for the herbicides.

Several conventions are used in the following Examples to simplify the data tables and discussions. Abbreviations are utilized to designate the location and type of trial (Loc-Type), the names of the microbial herbicides, and the names of the weeds. These abbreviations will be described below.

Experiments are separated by location and type of trial. The location abbreviations and corresponding description are: CA--California, FL--Florida, IL--Illinois, ML-Montreal, VT--Vermont. The control of environment is indicated by the type of trial: C--controlled environment growth chamber (highly controlled environment, temperature and light); G--greenhouse conditions (moderate control of temperature, little control of light); F--field conditions (no control of temperature, light, or relative humidity).

California: CA-G. All trials with this designation indicate that the trial was conducted in California under greenhouse conditions. Weeds in the cotyledonary stage of growth were treated in a precision application chamber designed specifically to test the efficacy of chemical and microbial herbicides. The application chamber utilizes carbon dioxide to pressurize the test material. The test material is delivered to the plants through a standard flat fan spray nozzle (Tee Jet 8002, Spraying Systems Co., Wheaton, Ill.) at a carrier rate of 25 gal/A. After treatment, the plants are placed into a mist chamber for 7 to 14 days. The percentage of plants which are dead or severely damaged (unlikely to survive) is recorded as percent weed control.

Florida: FL-F. The Florida field trial was carried out under permits from the USDA and the State of Florida. The test materials were applied in the morning and the trial was irrigated at dusk. Applications were made with the aid of a field backpack sprayer calibrated to apply 25 gal/A.

Illinois: IL-F. The Illinois field trial was carried out under permits from the USDA and the state of Illinois. The test materials were applied with the aid of a field backpack sprayer calibrated to apply 50 gal/A. Plants were treated in the four leaf stage of growth.

Montreal: ML-C. Weeds in the cotyledon, one, or two leaf stage of development were treated with solutions of test material to run-off. The rate of compounds in the spray solutions was based upon an application volume of 100 gal/A. Inoculated plants were placed into a dew chamber for 18 hr, then removed and placed in a controlled environment chamber. Evaluations were made after 20 to 45 days and the percentage of the total number of plants which were killed was recorded as percent weed control.

Montreal: ML-G. Weeds in the cotyledon, one, or two leaf stage of development were treated with solutions of test material to run-off. The rate of compounds in the spray solutions were based upon an application volume of 100 gal/A. Inoculated plants were placed into a dew chamber for 18 hr, then removed and placed in a controlled environment chamber. Evaluations were made after 20 to 45 days and the percentage of the total number of plants which were killed was recorded as percent weed control.

Montreal: ML-F. Field grown weeds in the cotyledon, one, or two leaf stage of development were treated with the test compounds in situ. Applications were made in a carrier volume of 100 gal/A. The percentage of the total number of plants which were killed was recorded as percent weed control.

Vermont: VT-F. Trials were applied using the same techniques described in the Montreal field trials (ML-F).

The weed abbreviations listed below are those accepted and reported in the Composite List of Weeds, Weed Science (1984) 2:Supp. 2.
ABUTH=*Abutilon theophrasti* Medik.
CASOB=*Cassia obtusifolia* L.
DEDTO=*Desmodium tortuosum* (Sw.) DC.

The abbreviations used for the microbial herbicides have been presented previously but will be duplicated here.
AC=*Alternaria cassiae*
CC=*Colletotrichum coccodes*
CT=*Colletotrichum truncatum*
FL=*Fusarium lateritium*

Following are examples which illustrate the products and procedures, including the best mode, for practicing the invention. These examples should not be construed as limiting.

EXAMPLE 1

Basagran in Combination with AC, CC, CT, and FL

Basagran is a herbicide of broadleaf plants. This herbicide is a sodium salt of an organic acid. Basagran reduced the germination of spores of AC and CT (Table 5) in addition to slowing the growth of CC (Table 6). Basagran produces synergistic activity in controlling weeds when mixed with microbial herbicides, in spite of the apparent detrimental effect of this herbicide on the germination and growth of the microbial herbicides.

The weed control activity of AC and FL was zero when these microbial herbicides were applied alone in these experiments. This lack of activity indicates that the environmental conditions during the experiment were restrictive to disease development. The activity of the AC and FL is greatly increased, even under these restrictive environmental conditions, by addition of the chemical herbicide.

With regard to the tables in this Example and the Examples following, application rates for microbial herbicides are expressed as PPA (propagules per acre) $\times 10^9$. Application rates for chemicals are expressed as pounds of active ingredient per acre.

| Microbial Herbicide | Weed | Trial Loc-Type | Application Rate Microbial | Application Rate Chemical | Percent weed control Microbial | Percent weed control Chemical | Tank mix |
|---|---|---|---|---|---|---|---|
| AC | CASOB | CA-G | 0.57 | 0.05 | 0 | 0 | 86 |
| CC | ABUTH | IL-F | 4100.00 | 0.75 | 10 | 13 | 65 |
| CC | ABUTH | ML-C | 4100.00 | 0.30 | 67 | 8 | 92 |
| CC | ABUTH | VT-F | 4100.00 | 0.75 | 7 | 40 | 79 |
| CT | DEDTO | CA-G | 9.30 | 0.30 | 41 | 0 | 71 |
| FL | ABUTH | CA-G | 410.00 | 0.05 | 0 | 38 | 65 |

The interaction reported in this Example was observed with a number of chemical herbicides which are salts of organic acids. Salts of organic acids frequently act as buffers in biological systems by maintaining the concentration of dissolved gasses and ions (e.g., the pH, which is the hydrogen ion concentration). A bicarbonate buffering system maintains the pH and $CO_2$ content of human blood plasma at the correct levels. The buffering capacity of organic acids and their salts is due to the disassociation of the proton, metallic ion or other inorganic ions in aqueous solution. Salts of chemical herbicides are likely to act as buffers whenever they occur in aqueous solution, and, more importantly, when they are mixed with microbial herbicides. In a chemically buffered environment, the microbial herbicide may be able to infect the weed and cause disease under environmental conditions which would otherwise be restrictive.

In addition to the buffering capacity described above, salts of organic acids (the salt, the ionized acid, or the ion released by the salt) may also act on the plant or pathogen to produce the synergistic interaction observed in this Example.

Salts of chemical herbicide compounds can be formed from metal cations in combination with the herbicidally active anion. Preferred metal cations are alkali metal cations, for example, lithium, sodium, potassium, cessium, and rubidium; and alkaline earth metal cations, for example, magnesium, calcium, strontium and barium. Other metal cations which can be used to form salts of chemical herbicide compounds are the heavy metal cations, for example, copper, silver, mercury, zinc, cadmium, chromium, manganese, iron, cobalt, nickel, aluminum, tin, and lead.

Salts of chemical herbicide compounds also can be formed from onium cations, for example, ammonium cations, sulfonium and sufoxonium cations and phosphonium cations.

In general, the subject invention includes any salt of an organic acid chemical herbicide compound. Advantageously, the salt form used should be soluble or suspensible in the herbicidal formula mixture. The formation of such salts is well known to persons skilled in the chemical herbicide art.

EXAMPLE 2

Blazer in Combination with AC, CC, CT, and FL

Blazer is another example of broadleaf chemical herbicide which is a salt of an organic acid. The environmental conditions during a majority of the experiments was limiting and the microbial herbicides demonstrated little or no weed control activity on their respective hosts. The inhibition of AC and CT spore germination and the reduction in growth of CC was much less than observed with the combinations with Basagran.

| Microbial Herbicide | Weed | Trial Loc-Type | Application rate Microbial | Application rate Chemical | Percent weed control Mircrobial | Percent weed control Chemical | Percent weed control Tank mix |
|---|---|---|---|---|---|---|---|
| AC | CASOB | CA-G | 0.57 | 0.05 | 0 | 0 | 86 |
| CC | ABUTH | VT-F | 4100.00 | 0.40 | 7 | 43 | 62 |
| CT | DEDTO | CA-G | 9.3 | 0.05 | 0 | 0 | 94 |
| FL | ABUTH | CA-G | 410.00 | 0.05 | 0 | 0 | 20 |

EXAMPLE 3

Classic in Combination with AC, CC, and CT

Classic is a broadleaf herbicide which is an ester. This herbicide is clearly antagonistic to the activity of AC when the mixture is applied to control sicklepod. Classic does not severely inhibit the spore germination of AC, indicating that the antagonistic interactions is possible affecting the physiology of the interaction between AC and the sicklepod plant. An example might indicate interference with stomatal opening which would make penetration of AC into the leaf more difficult.

Classic is synergistic in controlling weeds when applied in combination with CC, or CT. Both of these fungi are capable of penetrating the leaf directly (without the need for a wound or open stomates).

| Microbial Herbicide | Weed | Trial Loc-Type | Application rate Microbial | Application rate Chemical | Percent weed control Microbial | Percent weed control Chemical | Percent weed control Tank mix |
|---|---|---|---|---|---|---|---|
| AC | CASOB | CA-G | 0.29 | 0.02 | 31 | 4 | 21 |
| CC | ABUTH | ML-C | 4100.00 | 0.01 | 0 | 0 | 58 |
| CC | ABUTH | ML-F | 4100.00 | 0.02 | 0 | 8 | 37 |
| CT | DEDTO | FL-F | 31.00 | 0.02 | 0 | 16 | 49 |

EXAMPLE 4

Fusilade in Combination with AC and CT

Fusilade is a chemical herbicide which has activity in controlling monocots. Fusilade is a salt of an organic acid. This formulation should yield some environmental buffering capacity. However, the synergistic activity of this compound and AC and CT was not predictable. Fusilade was stimulatory to germination of AC spores but inhibitory to spores of CT (Table 5). Fusilade has no visible effect upon sicklepod or Florida beggarweed when applied alone.

| Microbial Herbicide | Weed | Trial Loc-Type | Application rate Microbial | Application rate Chemical | Percent weed control Microbial | Percent weed control Chemical | Percent weed control Tank mix |
|---|---|---|---|---|---|---|---|
| AC | CASOB | CA-G | 1.5 | 0.08 | 21 | 8 | 100 |
| CT | DEDTO | CA-G | 9.3 | 0.06 | 0 | 21 | 100 |

EXAMPLE 5

Hoelon in Combination with AC and CT

Hoelon is another chemical herbicide which has activity in controlling monocot weeds. Like Fusilade, Hoelon is a salt of an organic acid. Unlike Fusilade, Hoelon almost completely inactivates CT as a microbial herbicide by preventing spore germination (Table 5). The nature of the inactivation (cidal or static) has not been determined. In contrast to this interaction, AC demonstrates a synergistic response in controlling sicklepod when applied in combination with Hoelon.

| Microbial Herbicide | Weed | Trial Loc-Type | Application rate Microbial | Application rate Chemical | Percent weed control Microbial | Percent weed control Chemical | Percent weed control Tank mix |
|---|---|---|---|---|---|---|---|
| AC | CASOB | CA-G | 0.57 | 0.25 | 0 | 4 | 61 |
| CT | DEDTO | CA-G | 9.3 | 0.25 | 0 | 0 | 0 |

EXAMPLE 6

Poast in Combinatio with AC and CT

Poast, another monocot herbicide, is a ketone. The interaction of this herbicide with AC for control of sicklepod is dramatic. Neither the fungus nor the chemical demonstrated any control when applied alone. Poast may be capable of stabilizing the environment, modifying the physiology of the fungus, modifying the response of the host, or the pathogen was capable of modifying the activity of the herbicide.

Poast considerably reduced the germination of AC spores. The spores of CT were completely inhibited. The response of CT spores to Hoelon and Poast is similar.

| Microbial Herbicide | Weed | Trial Loc-Type | Application rate | | Percent weed control | | |
|---|---|---|---|---|---|---|---|
| | | | Microbial | Chemical | Microbial | Chemical | Tank mix |
| AC | CASOB | CA-G | 0.57 | 0.05 | 0 | 0 | 100 |
| CT | DEDTO | CA-G | 9.3 | 0.01 | 7 | 0 | 18 |

EXAMPLE 7

Scepter in Combination with AC and CT

Scepter, a broadleaf herbicide, is a salt of an organic acid. Refer to Example 1 for a discussion of the possible interactions between microbial herbicides and salts of chemical herbicides. Scepter alone has some herbicidal activity against sicklepod. However, the combination of the microbial and chemical herbicides provides greatly enhanced, synergistic, control of sicklepod. The activity of CT and Scepter for control of Florida beggarweed is not as dramatic as that demonstrated with AC. Neither the CT nor Scepter were capable of damaging Florida beggarweed alone. The combination killed one third of the weeds.

extra nutrition for the fungus and increases its rate of growth. In addition to the increase of growth and activity of the fungus, the plant has been damaged and is therefore crippled in its ability to defend against the fungal invasion.

The chemical herbicide Paraquat is another non-selective herbicide. This herbicide is known to damage the plant cuticle. If the trend in interactions presented in this disclosure is maintained with further testing, this herbicide should provide a combination of cuticular damage in addition to its biological buffering capabilities. The interaction should be synergistic.

Also note that both of these compounds stimulated the germination of AC and CT spores (Table 5).

| Microbial Herbicide | Weed | Trial Loc-Type | Application rate | | Percent weed control | | |
|---|---|---|---|---|---|---|---|
| | | | Microbial | Chemical | Microbial | Chemical | Tank mix |
| AC | CASOB | CA-G | 1.10 | 0.06 | 0 | 29 | 100 |
| CT | DEDTO | CA-G | 9.3 | 0.03 | 7 | 92 | 82 |

EXAMPLE 9 Surflan in combination with AC and CT.

| Microbial Herbicide | Weed | Trial Loc-Type | Application rate | | Percent weed control | | |
|---|---|---|---|---|---|---|---|
| | | | Microbial | Chemical | Microbial | Chemical | Tank mix |
| AC | CASOB | CA-G | 0.29 | 0.01 | 31 | 17 | 76 |
| CT | DEDTO | CA-G | 31.00 | 0.15 | 0 | 0 | 33 |

EXAMPLE 8

Sencor in Combination with AC and CT

Refer to the discussion of EXAMPLE 8 for an interpretation of the results in this Table.

| Microbial Herbicide | Weed | Trial Loc-Type | Application rate | | Percent weed control | | |
|---|---|---|---|---|---|---|---|
| | | | Microbial | Chemical | Microbial | Chemical | Tank mix |
| AC | CASOB | CA-G | 1.5 | 2.60 | 21 | 14 | 75 |
| CT | DEDTO | CA-G | 9.3 | 0.50 | 0 | 13 | 100 |

Sencor and Surflan (Example 9) are non-selective herbicides which are normally applied to fields as a preplant treatment. Sencor and Surflan cannot be applied as post emergence herbicides because they are phytotoxic to most field crops at the rates needed to eliminate the weeds. The interaction between these herbicides and microbial herbicides in controlling weeds is probably a result of increased exudation by the host. Sencor and Surflan will damage some of the cells of the sicklepod when applied at the low rates used in Examples 8 and 9. However, this damage is not enough to significantly reduce the growth and development of sicklepod. The damage is enough to cause cuticular wounds and leakage of cellular contents. This increase in exudation (actually uncontrolled release) provides

EXAMPLE 10

Plant Growth Regulator B-Nine in Combination wih AC and CT

The plant growth regulators (PGR) B-Nine and Dropp (Example 11) were neither synergistic nor antagonistic when applied in combination with AC. However, both of these PGR's demonstrated synergy when applied with a Colletotrichum sp. (CC and CT). The compounds may be affecting the fungi to make them more aggressive, or inducing the host to become more susceptible (by interference with the host physical and biochemical defenses). Both of these PGR's tend to make the plant short and grow abnormally.

| Microbial Herbicide | Weed | Trial Loc-Type | Application rate | | Percent weed control | | |
|---|---|---|---|---|---|---|---|
| | | | Microbial | Chemical | Microbial | Chemical | Tank mix |
| AC | CASOB | CA-G | 0.57 | 0.05 | 0 | 0 | 7 |

-continued

| Microbial Herbicide | Weed | Trial Loc-Type | Application rate | | Percent weed control | | |
|---|---|---|---|---|---|---|---|
| | | | Microbial | Chemical | Microbial | Chemical | Tank mix |
| CT | DEDTO | CA-G | 42.00 | 0.40 | 23 | 63 | 100 |

EXAMPLE 11

Plant Growth Regulator Dropp in Combination with AC, CC, and CT

Refer to Example 10 for a discussion of the activity of this compound.

| Microbial Herbicide | Weed | Trial Loc-Type | Application rate | | Percent weed control | | |
|---|---|---|---|---|---|---|---|
| | | | Microbial | Chemical | Microbial | Chemical | Tank mix |
| AC | CASOB | CA-G | 1.10 | 0.10 | 0 | 0 | 0 |
| CC | ABUTH | ML-C | 4100.00 | 0.07 | 0 | 0 | 42 |
| CC | ABUTH | ML-C | 4100.00 | 0.14 | 17 | 0 | 67 |
| CC | ABUTH | ML-G | 4100.00 | 0.07 | 0 | 0 | 67 |
| CT | DEDTO | CA-G | 9.3 | 0.03 | 23 | 42 | 100 |

EXAMPLE 12

Plant Growth Regulator Embark in Comination with AC and CT

Embark is a plant growth regulator which demonstrates synergy when applied in combination with AC and CT. Unlike B-Nine and Dropp (Examples 10 and 11) Embark is a salt of an organic acid. Refer to Example 1 for a discussion of the possible interactions of organic salts and microbial herbicides.

| Microbial Herbicide | Weed | Trial Loc-Type | Application rate | | Percent weed control | | |
|---|---|---|---|---|---|---|---|
| | | | Microbial | Chemical | Microbial | Chemical | Tank mix |
| AC | CASOB | CA-G | 1.1 | 0.05 | 0 | 0 | 73 |
| CT | DEDTO | CA-G | 9.3 | 0.25 | 23 | 0 | 100 |

EXAMPLE 13

*C. malvarum*, disclosed in U.S. Pat. No. 3,999,973, can be used in combination with a chemical herbicide or plant growth regulator, as disclosed herein, to control the growth of prickly sida (*Sida spinosa* L.) or teaweed.

EXAMPLE 14

*Fusarium lateritium*, disclosed in U.S. Pat. No. 4,419,120, can be used in combination with a chemical herbicide or plant growth regulator, as disclosed herein, to control the growth of prickly sida, velvet-leaf, and spurred anoda.

EXAMPLE 15

*C. gloeosporioides* f. sp. *aeschynomene*, disclosed in U.S. Pat. No. 3,849,104, can be used in combination with a chemical herbicide or plant growth regulator, as disclosed herein, to control the growth of northern jointvetch.

EXAMPLE 16

Upon using a mixture of two or more chemical herbicides or plant growth regulators, as disclosed herein, in a mixture with a microbial herbicide which is a plant pathogen for a target weed, as disclosed herein, there is obtained multiple weed control.

The Examples presented herein show synergy with salts of chemical herbicides and plant growth regulators in mixture with microbial herbicides where the salt is compatible with the microbial herbicide.

We claim:

1. A composition for controlling Florida beggarweed comprising an effecive amount of the fungal pathogen *Colletotrichum truncatum*, and a chemical herbicide selected from the group consisting of bentazon sodium salt, acifluorfen sodium salt, fluazifop, and oryzalin.

2. The composition according to claim 1 wherein the chemical herbicide is bentazon sodium salt.

3. The composition according to claim 1 wherein the chemical herbicide is acifluorfen sodium salt.

4. The composition according to claim 1 wherein the claimed herbicide is fluazifop.

5. The composition according to claim 1 wherein the chemical herbicide is oryzalin.

6. A process for controlling Florida beggarweed comprising the application of an effective amount of a synergistic herbidical composition of *Colletotrichum truncatum*, and a chemical herbicide selected from the group consisting of bentazon sodium salt, acifluorfen sodium salt, fluazifop, and oryzalin.

7. The process of claim 6 wherein the chemical herbicide is bentazon sodium salt.

8. The process of claim 6 wherein the chemical herbicide is acifluorfen sodium salt.

9. The process of claim 6 wherein the chemical herbicide is fluazifop.

10. The process of claim 6 wherein the chemical herbicide is oryzalin.

* * * * *

UNITED STATES PATENT AND TRADEMARK OFFICE
CERTIFICATE OF CORRECTION

PATENT NO. : 4,775,405
DATED : October 4, 1988
INVENTOR(S) : Jerry D. Caulder, Larry Stowell It is certified that error appears in the above-identified patent and that said Letters Patent are hereby corrected as shown below:

Title page, line 3,

| | |
|---|---|
| Abstract: | "colletotrichum truncatum" should read —Colletotrichum truncatum—. |
| Column 5: | line 29: "numphaerum" should read —nymphaerum—. |
| Column 11: | line 24: "were" should read —was—. |
| Column 13: | line 4: "of broadleaf" should read —of a broadleaf—; line 46: "indicate" should read —include—. |
| Column 14: | line 46: "Combinatio" should read —Combination—. |
| Column 17: | line 25: "Comination" should read —Combination—. |

Signed and Sealed this

Seventh Day of March, 1989

*Attest:*

DONALD J. QUIGG

*Attesting Officer*     *Commissioner of Patents and Trademarks*